US006881875B2

(12) United States Patent
Swenson (10) Patent No.: US 6,881,875 B2
(45) Date of Patent: Apr. 19, 2005

(54) FOAM/FILM COMPOSITE MEDICAL ARTICLES

(75) Inventor: Mary M. Swenson, St. Paul, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 10/351,932

(22) Filed: Jan. 27, 2003

(65) Prior Publication Data

US 2003/0125685 A1 Jul. 3, 2003

Related U.S. Application Data

(62) Division of application No. 09/507,107, filed on Feb. 17, 2000, now Pat. No. 6,548,727.

(51) Int. Cl.$^7$ ............................................. A61F 13/00
(52) U.S. Cl. .................................... 602/46; 602/41
(58) Field of Search ................... 602/41–59; 128/888, 128/889

(56) References Cited

U.S. PATENT DOCUMENTS

| | | |
|---|---|---|
| RE24,906 E | 12/1960 | Ulrich |
| 3,975,567 A | 8/1976 | Lock |
| 3,978,855 A | 9/1976 | McRae et al. |
| 4,499,896 A | 2/1985 | Heinecke |
| 4,541,426 A | 9/1985 | Webster |
| 4,561,435 A | 12/1985 | McKnight et al. |
| 4,595,001 A | 6/1986 | Potter et al. |
| 4,598,004 A | 7/1986 | Heinecke |
| 4,747,401 A | 5/1988 | Potter et al. |
| 4,753,231 A * | 6/1988 | Lang et al. .................. 602/47 |
| 4,798,201 A | 1/1989 | Rawlings et al. |
| 4,833,179 A | 5/1989 | Young et al. |
| 4,871,812 A | 10/1989 | Lucast et al. |
| 4,897,982 A | 2/1990 | Day et al. |

(Continued)

FOREIGN PATENT DOCUMENTS

| | | | |
|---|---|---|---|
| DE | 2 319 706 | 11/1973 | ........... C08G/22/44 |
| DE | 26 21 126 | 11/1976 | ........... C08G/18/80 |
| EP | 0 171 268 B1 | 2/1986 | ........... A61F/13/00 |
| WO | WO 99/47090 | 9/1999 | ........... A61F/13/15 |

OTHER PUBLICATIONS

American Society of Testing Materials, "ASTM E–96–80, Standard Test Methods for Water Vapor Transmission of Materials," *Annual Book of ASTM Standards*, pp. 682–691 (1981).

Wente et al., "Manufacture of Superfine Organic Fibers," Report No. 4364 of the Naval Research Laboratories, Washington, DC, Title page, publication page, abstract, table of contents, and pp. 1–15 (1954).

Wente, "Superfine Thermoplastic Fibers," *Industrial Engineering Chemistry*, 48:1342–1346(1956).

"Polycril™ Foams," Fulflex Polycril Foams, http://www-.fulflex.com/pages/polycrilfoams.html, 2 pages, available on line on or before Dec. 15, 1999.

Lopez, N.; "Enhanced Hydrophilic Polyurethane Prepolymers for Consumer and Industrial Applications"; Product brochure from The Dow Chemical Company; Aug. 2001 (8 pgs.)

Primary Examiner—Kim M. Lewis
(74) *Attorney, Agent, or Firm*—Nancy M. Lambert (57) ABSTRACT

The present invention provides medical articles, such as wound dressings. In one embodiment, the medical article includes a backing, an absorbent foam, and a fibrous adhesive disposed between the backing and the absorbent foam, wherein the backing includes a liquid-impervious, moisture-vapor permeable polymeric film. In another embodiment, the medical article includes a backing, an absorbent, substantially nonswellable foam, and an adhesive disposed therebetween. In yet another embodiment, the medical article includes a backing, a foam, and a fibrous adhesive disposed therebetween.

10 Claims, 1 Drawing Sheet

U.S. PATENT DOCUMENTS

| | | | |
|---|---|---|---|
| 4,906,240 A | 3/1990 | Reed et al. | |
| 4,917,928 A | 4/1990 | Heinecke | |
| RE33,353 E | 9/1990 | Heinecke | |
| 5,000,172 A | 3/1991 | Ward | |
| 5,064,653 A | 11/1991 | Sessions et al. | |
| 5,065,752 A | 11/1991 | Sessions et al. | |
| 5,088,483 A | 2/1992 | Heinecke | |
| 5,098,500 A | 3/1992 | Reed et al. | |
| 5,160,315 A | 11/1992 | Heinecke et al. | |
| 5,183,664 A | 2/1993 | Ansell | |
| 5,230,701 A | 7/1993 | Meyer et al. | |
| 5,254,301 A | 10/1993 | Sessions et al. | |
| 5,271,943 A | 12/1993 | Bogart et al. | |
| 5,292,777 A * | 3/1994 | DesMarais et al. | 521/64 |
| 5,328,450 A | 7/1994 | Smith et al. | |
| 5,409,472 A | 4/1995 | Rawlings et al. | |
| 5,512,041 A | 4/1996 | Bogart | |
| 5,520,629 A | 5/1996 | Heinecke et al. | |
| 5,531,855 A | 7/1996 | Heinecke et al. | |
| 5,648,166 A | 7/1997 | Dunshee | |
| 5,650,450 A | 7/1997 | Lovette et al. | |
| 5,653,699 A | 8/1997 | Reed et al. | |
| 5,695,777 A | 12/1997 | Donovan et al. | |
| 5,738,642 A | 4/1998 | Heinecke et al. | |
| 5,744,509 A | 4/1998 | Wilson et al. | |
| 5,750,444 A * | 5/1998 | Jarrell et al. | 442/62 |
| 5,782,787 A | 7/1998 | Webster | |
| 5,849,325 A | 12/1998 | Heinecke et al. | |
| 5,908,693 A | 6/1999 | Delgado et al. | |
| 5,947,917 A | 9/1999 | Carte et al. | |
| 6,019,996 A | 2/2000 | Cheong | |
| 6,326,410 B1 | 12/2001 | Cheong | 521/67 |
| 6,410,464 B1 * | 6/2002 | Menzies et al. | 442/151 |
| 6,548,727 B1 * | 4/2003 | Swenson | 602/41 |

* cited by examiner

FOAM/FILM COMPOSITE MEDICAL ARTICLES

CROSS REFERENCE TO RELATED APPLICATIONS

This application is a division of U.S. patent application Ser. No. 09/507,107, filed Feb. 17, 2000 now U.S. Pat. No. 6,548,727.

FIELD OF THE INVENTION

The present invention is directed to medical articles, such as wound dressings. Such articles are useful in the treatment of skin lesions, for example.

BACKGROUND OF THE INVENTION

Wound dressings should preferably absorb exudate from lesions without adhering to wound surfaces or floating away from the wound surface. Adhesion problems can occur when the wound has dried out due to the lack of production of exudate. Attempts to remove the dressing will result in disturbance of the newly forming layer of the skin over the wound and hence wound healing is delayed. The problem of dressings that float away from exuding lesions typically occurs when the wound produces particularly large volumes of exudate. Solutions to such problems involve, for example, using a continuous layer that retards the rate of loss of water, thereby preventing adhesion of the dressing to the wound, or providing the dressing with holes so that the exudate can pass through the holes to an absorbent, thereby keeping the dressing in contact with the wound.

It is desirable for effective wound healing to have wound dressings that do not allow the wound to dry out completely and that do not allow exudate to pool. Thus, a breathable wound dressing is desired that can absorb exudate, but not allow the wound to dry out. There are known wound dressings that include foams that attempt to address these problems; however, these dressings can have problems with breathability and swelling of the foam, which can place pressure on the wound, or alternatively, with poor absorption of exudate.

Thus, many of the known wound dressings are not free of disadvantages since what may be an excellent dressing for one kind of wound will be unsuitable for many other wounds because of the differences in the output of exudate. Thus, additional wound dressings are still needed that are suitable for use on a number of different wound types.

SUMMARY OF THE INVENTION

The present invention provides medical articles, such as wound dressings. In one embodiment, the medical article includes a backing, an absorbent foam, and a fibrous adhesive disposed between the backing and the absorbent foam, wherein the backing includes a liquid-impervious, moisture-vapor permeable polymeric film. In another embodiment, the medical article includes a backing, an absorbent, substantially nonswellable foam, and an adhesive disposed therebetween. In yet another embodiment, the medical article includes a backing, a foam, and a fibrous adhesive disposed therebetween.

Preferably, the medical articles have a dry MVTR of less than about 2000 g/m$^2$/24 hours and a wet MVTR of at least about 3000 g/m$^2$/24 hours at 38° C. and 20% relative humidity. Preferably, the medical articles have a wet MVTR of at least about 5000 g/m$^2$/24 hours at 38° C. and 20% relative humidity.

Preferably, the liquid-impervious, moisture-vapor permeable polymeric film has a dry MVTR of at least about 300 g/m$^2$/24 hours at 38° C. and 20% relative humidity. Preferably, it has a wet MVTR of at least about 3000 g/m$^2$/24 hours at 38° C. and 20% relative humidity. For certain embodiments, the liquid-impervious, moisture-vapor permeable polymeric film comprises one or more layers. Preferably, the liquid-impervious, moisture-vapor permeable polymeric film is a thermoplastic polyurethane.

The foam is preferably absorbent and absorbs greater than 250 wt-% aqueous saline solution when immersed in phosphate buffered saline containing 0.9 wt-% NaCl at 37° C. for 30 minutes. Preferably, the foam is also substantially non-swellable and increases in volume by no greater than about 10% following a 30-minute soaking in phosphate buffered saline at 37° C. For certain preferred embodiments the foam is an open cell foam. Preferably, the foam is a polyurethane foam.

For certain embodiments, the backing includes a liquid-impervious, moisture-vapor permeable polymeric film and a nonwoven web. The liquid-impervious, moisture-vapor permeable polymeric film can be disposed between the nonwoven web and the foam, or the nonwoven web can be disposed between the liquid-impervious, moisture-vapor permeable polymeric film and the foam. The moisture-vapor polymeric film can be bonded to the nonwoven web with a fibrous adhesive, such as a polyacrylate fibrous adhesive, or thermomechanically, for example.

DETAILED DESCRIPTION OF PREFERRED EMBODIMENTS

The present invention is directed to medical articles, such as wound dressings that are useful in the treatment of skin lesions, for example. Other uses of medical articles of the present invention include, for example, diapers and medical padding such as liposuction padding, hygiene pads, corn and callous pads, toe cushioning pads, ostomy pads, and pads for protecting and cushioning tube sites such as tracheotomy tubes.

Medical articles of the present invention include a backing, preferably a liquid-impervious, moisture-vapor permeable polymeric film, a foam, preferably an absorbent foam, and more preferably an absorbent, substantially non-swellable foam, and an adhesive disposed therebetween. As used herein, a "foam" refers to a cellular polymeric structure, preferably an open-cell foam. The foam may be in discrete islands such that the foam is not coextensive with the backing.

Medical articles of the present invention are capable of absorbing aqueous saline solutions, hence they are capable of absorbing exudate. Preferably, they can absorb greater than 250 weight percent (wt-%), more preferably at least about 500 wt-%, and most preferably at least about 800 wt-%, aqueous saline solution based on the dry weight of the article. Typically, these values are obtained using a saline absorbency test in which a dry, weighed sample is immersed for 30 minutes at 37° C. in phosphate-buffered saline containing 0.9 wt-% NaCl.

Significantly, medical articles of the present invention typically have a relatively low dry moisture vapor transmission rate (MVTR) and a relatively high wet MVTR. This is important to allow the wound under the dressing to heal under moist conditions without causing the skin surrounding the wound to become macerated.

Herein, dry MVTR is measured by ASTM E-96-80 (American Society of Testing Materials) at 38° C. and 20% relative humidity using an upright cup method, and wet MVTR is measured by a similar method except that the sample jars are inverted so the water is in direct contact with the test sample. Preferably, medical articles of the present invention have a dry MVTR of less than about 2000 g/m$^2$/24 hours, more preferably less than about 1800 g/m$^2$/24 hours, and most preferably less than about 1500 g/m$^2$/24 hours. Preferably, they also have a wet moisture vapor transmission rate of at least about 3000 g/m$^2$/24 hours, more preferably at least about 5000 g/m$^2$/24 hours, even more preferably at least about 7500 g/m$^2$/24 hours, and most preferably at least about 10,000 g/m$^2$/24 hours.

The backing typically includes a liquid-impervious, moisture-vapor permeable polymeric film, although it can include a variety of other materials, which are preferably used in combination with a liquid-impervious, moisture-vapor permeable polymeric film. The liquid-impervious, moisture-vapor permeable polymeric film is a conformable organic polymeric material that preferably retains its structural integrity in a moist environment. Herein, "conformable" films are those that conform to a surface, even upon movement of the surface, as with the surface of a body part. Suitable films have a composition and thickness that allow for the passage of moisture vapor through them. The film aids in the regulation of water vapor loss from the wound area beneath the dressing. The film also acts as a barrier to both bacteria and to liquid water or other liquids.

The moisture-vapor permeable polymeric films can be of a wide range of thicknesses. Preferably, they are at least about 10 microns (micrometers) thick, and more preferably at least about 12 microns thick. Preferably, they are no greater than about 250 microns, and more preferably no greater than about 75 microns thick. Furthermore, they can include one or more layers tailored to have the desired properties. These layers can be coextruded and/or bonded together with adhesive layers, for example, as long as the overall properties of the film and article, as described herein, are met.

Preferably, suitable films for use in the medical articles of the present invention have differential moisture vapor transmission properties. Preferably, a suitable film has a dry MVTR that is less than the film's wet MVTR. Preferably, suitable films have a dry MVTR of at least about 300 g/m$^2$/24 hours and a wet MVTR of at least about 3000 g/m$^2$/24 hours. The films can be tested using the same methods described above for the article.

Examples of suitable materials for the liquid-impervious, moisture-vapor permeable polymeric films include synthetic organic polymers including, but not limited to: polyurethanes commercially available from B. F. Goodrich, Cleveland, Ohio, under the trade designation ESTANE, including ESTANE 58237 and ESTANE 58245; polyether-amide block copolymers commercially available from Elf Atochem, Philadelphia, Pa., under the trade designation PEBAX, including PEBAX MV 1074; polyether-ester block copolymers commercially available from DuPont, Wilmington, Del., under the trade designation HYTREL. The polymeric films can be made of one or more types of monomers (e.g., copolymers) or mixtures (e.g., blends) of polymers. Preferred materials are thermoplastic polymers (e.g., those that soften when exposed to heat and return to their original condition when cooled). A particularly preferred material is a thermoplastic polyurethane.

Backings of the medical articles of the present invention can also include other breathable materials including, for example, nonwoven, woven, and knit webs, porous films (e.g., provided by perforations or microporous structure), foams, paper, or other known backings. A preferred backing includes a combination of a liquid-impervious, moisture-vapor permeable polymeric film and a moisture-vapor permeable nonwoven web that can, among other advantages, impart enhanced structural integrity and improved aesthetics to the dressings. These layers of film and web may or may not be coextensive. A preferred such nonwoven web is a melt processed polyurethane (such as that available under the trade designation MORTHANE PS-440 from Morton International, Seabrook, N.H.), or hydroentangled nonwoven polyester or rayon-polyester webs (such as those available under the trade designation SONTARA 8010 or SONTARA 8411 from DuPont, Wilmington, Del.).

The layers within the backing are preferably bonded together using an adhesive layer, for example, that can be continuous or discontinuous (e.g., such as that produced with a pattern-coated adhesive layer), although other means of bonding can be used including thermomechanical bonding, such as thermal bonding or ultrasonic welding. Suitable adhesives for use on the backing can be any of those useful for wound dressings, such as those disclosed in International Publication Nos. WO 99/27975 and 99/28539 (both to Joseph, et al.) and in U.S. Pat. Nos. Re. 24,906 (Ulrich) and 5,849,325 (Heinecke, et al.). Preferably, the adhesive is a fibrous adhesive as disclosed in International Publication Nos. WO 99/27975 and 99/28539.

Briefly, such fibrous adhesives are formed from coherent pressure-sensitive adhesive fibers that are intimately entangled each with the other in the form of a coherent breathable fibrous adhesive nonwoven web. Suitable pressure-sensitive adhesive fiber webs can be formed as melt blown microfiber webs. Preferred microfine fibers are termed melt blown fibers and are generally substantially continuous and form into a coherent web by entanglement. Other such fibers can be formed by conventional melt spinning processes. Such adhesive fibers are typically 100 microns or less in diameter, and preferably about 50 microns or less. Preferred fibrous adhesives include polyacrylates. More preferred fibrous adhesives include those formed from polyacrylate copolymers and terpolymers, e.g., the polymer comprised of isooctyl polyacrylate, polyacrylic acid, and styrene macromer in a 92/4/4 wt-% ratio.

Medical articles of the present invention include a foam, preferably an absorbent foam, and more preferably an absorbent foam that is also a substantially nonswellable foam. In this context, an "absorbent" foam is one that is capable of absorbing saline water, and hence, exudate from a wound. Preferably, suitable foams are those that can absorb greater than 250%, more preferably at least about 500%, and most preferably at least about 800%, by weight aqueous saline solution based on the dry weight of the foam. Typically, these values are obtained using a saline absorbency test in which a dry, weighed sample is immersed for 30 minutes at 37° C. in phosphate-buffered saline containing 0.9 wt-% NaCl.

Preferred foams are also substantially nonswellable. In this context, "substantially nonswellable" means that there is little or no increase in volume of the foam upon absorption of water or saline, and hence, exudate from a wound. Preferably, suitable foams increase in volume by no greater than about 10%, and more preferably by no greater than about 5%, following a 30-minute soaking in phosphate buffered saline, as defined in the test method in the examples below, at 37° C.

The foams can be of a wide range of thicknesses. Preferably, they are at least about 0.5 millimeter, and more preferably at least about 1 millimeter thick. Preferably, they are no greater than about 80 millimeters, and more preferably no greater than about 30 millimeters thick. Furthermore, they can include one or more layers tailored to have the desired properties. These layers can be directly bonded to each other or bonded together with adhesive layers, for example, as long as the overall properties of the foam and article, as described herein, are met. Optionally, disposed between these layers can be one or more layers of polymeric netting or nonwoven, woven, or knit webs for enhancing the physical integrity of the foam.

Figure 3:
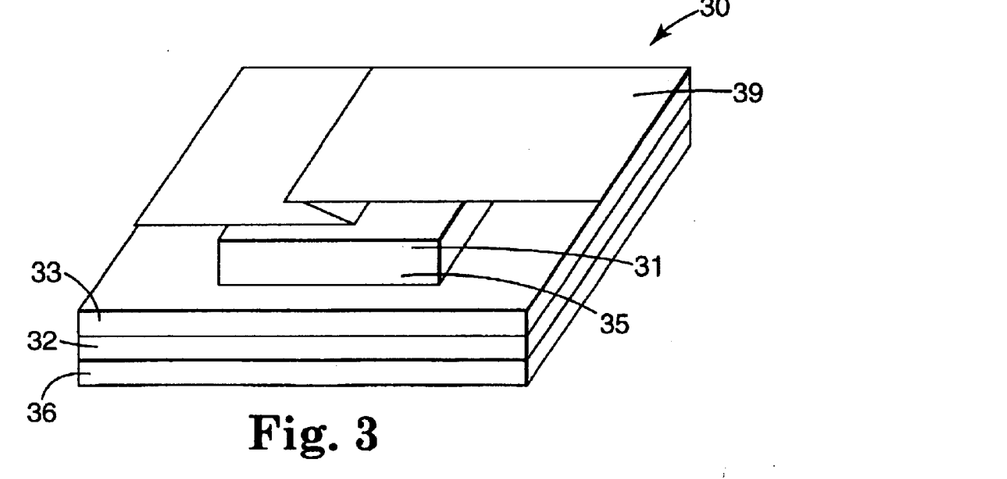
FIG. 3 is a representation of an embodiment of the present invention that includes a foam pad adhesively attached to a backing that includes a film and a nonwoven web with a second absorbent pad between the backing and the foam pad.

Furthermore, the medical article can optionally include other absorbent materials, such as superabsorbent fibers or particles, such as blended nonwoven rayon/"Oasis" superabsorbent fibers that are available from National Nonwovens, Cincinnati, Ohio. For example, a second absorbent pad (an internal pad) is shown in FIG. 3.

Suitable open cell foams preferably have an average cell size (typically, the longest dimension of a cell, such as the diameter) of at least about 30 microns, more preferably at least about 50 microns, and preferably no greater than about 800 microns, more preferably no greater than about 500 microns, as measured by scanning electron microscopy (SEM) or light microscopy. Such open cell foams when used in dressings of the present invention allow transport of fluid and cellular debris into and within the foam. Preferably, the foam includes a synthetic polymer that is adapted to form a conformable open cell foam that absorbs the wound exudate. Examples of suitable materials for the absorbent, substantially nonswellable foams include synthetic organic polymers including, but not limited to: polyurethanes, carboxylated butadiene-styrene rubbers, polyesters, and polyacrylates. The polymeric foams can be made of one or more types of monomers (e.g., copolymers) or mixtures (e.g., blends) of polymers. Preferred foam materials are polyurethanes. A particularly preferred foam is a polyurethane, available under the trade designation POLYCRIL 400 from Fulflex, Inc, Middleton, R.I.

Although suitable foams may be hydrophilic per se, they are preferably hydrophobic and treated to render them more hydrophilic, for example with surfactants such as nonionic surfactants, e.g., the oxypropylene-oxyethylene block copolymers available under the trade designation PLURONIC from BASF Wyandotte, Mount Olive, N.J. Use of foams, or surfactants incorporated therein, that possess a hydrophilic surface reduces the tendency for the exudate to coagulate rapidly in the foam. This helps to keep the wound in a moist condition even when production of exudate has ceased from the wound.

The backing is preferably bonded to the foam using an adhesive layer that can be continuous or discontinuous (e.g., a pattern-coated adhesive layer). Suitable adhesives for use on the backing can be any of those useful for wound dressings, such as those disclosed in International Publication Nos. WO 99/27975 and 99/28539 (both to Joseph, et al.) and in U.S. Pat. Nos. Re. 24,906 (Ulrich), 5,849,325 (Heinecke, et al.), and 4,871,812 (Lucast, et. al.). Preferably, the adhesive is a fibrous adhesive as disclosed in International Publication Nos. WO 99/27975 and 99/28539. Preferred fibrous adhesives include polyacrylates. More preferred fibrous adhesives include those formed from polyacrylate copolymers and terpolymers, e.g., the polymer comprised of isooctyl polyacrylate, polyacrylic acid, and styrene macromer in a 92/4/4 wt-% ratio.

Preferably, the backing will be coextensive with the foam, although in certain embodiments the backing (or at least one of the layers of the backing) will have a greater surface area than the surface area of the foam (i.e., the backing will extend beyond the periphery of the foam). For the latter embodiments, the backing can include an adhesive disposed on the surface to which the foam is bonded around the periphery of the foam for adhesion to a surface such as skin. Suitable adhesives for use around the periphery of the foam can be any of those that are compatible with skin and useful for wound dressings, such as those disclosed in U.S. Pat. Nos. Re. 24,906 (Ulrich), 5,849,325 (Heinecke, et al.), and 4,871,812 (Lucast, et. al.) (water-based and solvent-based adhesives); 4,833,179 (Young, et al.) (hot-melt adhesives); 5,908,693 (Delgado, et al.) (microsphere adhesives); International Publication Nos. WO 99/27975 and 99/28539 (both to Joseph, et al.) (low trauma fibrous adhesives); and, U.S. patent application Ser. Nos. 09/329,514 (Lucast, et al.), PCT/US99/13,866 (Lucast, et al.), and PCT/US99/13,865 (Gieselman) (wet-skin adhesives). The medical articles of the present invention can optionally include a wound-contacting layer bonded to the exposed surface of the foam (i.e., the surface opposite the surface to which the film is bonded). Examples of such wound-contacting layers include polymeric netting and porous (e.g., perforated) films, or other conventional materials that prevent the dressing from sticking to the wound. This wound-contacting layer can be bonded directly bonded to the foam (e.g., cast or thermomechanical bonding), or bonded to the foam using an adhesive layer, for example.

Figure 1:
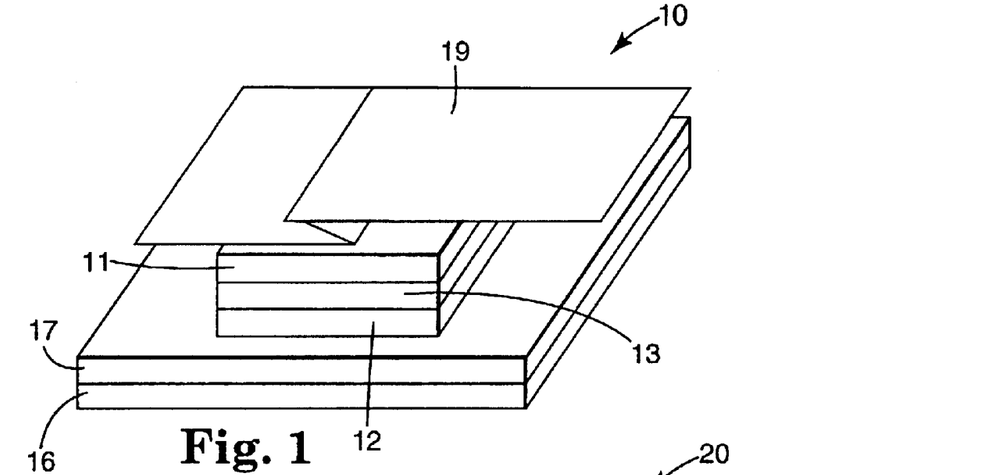
FIG. 1 is representation of an embodiment of the present invention that includes a foam pad adhesively attached to a film, which is adhesively attached to a nonwoven web.

Referring to the figures, certain preferred embodiments are specifically shown. FIG. 1 is representation of a medical dressing 10 that includes a foam pad 11 adhesively attached to a film 12 with an adhesive layer 13, which are all coextensive. This construction of foam/adhesive/film is adhesively attached to a nonwoven web 16 with an adhesive layer 17, both of which extend beyond the periphery of the foam/adhesive film construction. Herein, even though the film 12, adhesive 17, and nonwoven web 16 are not coextensive, they are referred to herein as the "backing" for the foam pad 11. Also shown is a liner 19, such as a J-fold liner, for example.

Figure 2:
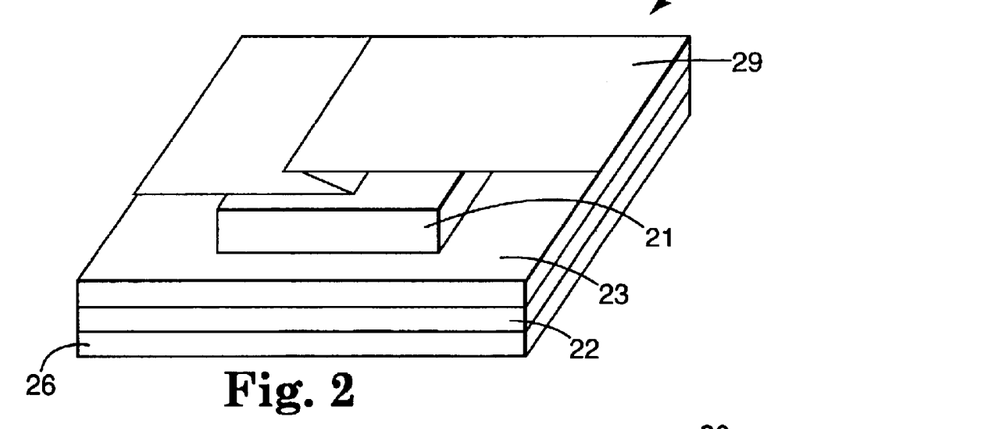
FIG. 2 is a representation of an embodiment of the present invention that includes a foam pad adhesively attached to a backing that includes a film and a nonwoven web.

FIG. 2 is a representation of a medical dressing 20 that includes a foam pad 21 adhesively attached to a film 22 with an adhesive layer 23. The film 22 is attached to a nonwoven web 26. The film 22, nonwoven web 26, and adhesive layer 23 are coextensive and extend beyond the periphery of the foam pad 21. Also shown is a liner 29.

FIG. 3 is a representation of a medical article 30 that includes a foam pad 31 and second absorbent pad 35 that are adhesively attached to a film 32 with an adhesive layer 33. The film 32 is attached to a nonwoven web 36. The film 32, nonwoven web 36, and the adhesive layer 33 are coextensive and extend beyond the periphery of the foam pad 31.

The medical articles of the invention can include graphics printed on the liquid-impervious, moisture-vapor permeable polymeric film. Suitable inks and methods of applying such graphics are disclosed in International Publication No. WO 99/19410 (Dunshee et al.). Such graphics can be placed on either major surface of the film.

The medical articles of the invention can contain a topically active medicament, such as an antibacterial agent. Preferably the antibacterial agent is a broad-spectrum antibacterial agent such as a silver salt, a sulphadiazine, an acceptable iodine source such as povidone iodine (also called polyvinyl pyrrolidone-iodine or PVP/I), chlorhexidine salts such as the gluconate, acetate, hydrochloride or the like salts or quaternary antibacterial agents such as benzalkonium chloride. Favored antibacterial agents include the salts of chlorhexidine. Preferably the medicament is present in the foam layer.

Typically, the medical articles of this invention are sterile and are provided sealed within a bacteria-proof package. The medical article may be rendered sterile by any suitable sterilization means, for example by gamma irradiation, steam sterilization, or ethylene oxide.

One process of manufacturing the dressings of the present invention is by sequential or simultaneous lamination of film, adhesive, foam, and optional nonwoven layers together at elevated temperatures. The films can be made from an appropriate thermoplastic resin by conventional extrusion processes, for example, as described in U.S. Pat. No. 4,499,896 (Heinecke). The film is generally supported on a standard release liner during the foam-casting operation.

Objects and advantages of this invention are further illustrated by the following examples, but the particular materials and amounts thereof recited in these examples, as well as other conditions and details, should not be construed to unduly limit this invention. Unless otherwise indicated, all parts and percentages are by weight.

EXAMPLES

Test Protocols

Saline Water Absorbency

Evaluation of saline water absorbency was measured using the following test procedure. A 5.1-cm×5.1-cm sample was immersed in phosphate-buffered saline (Sigma-Aldrich Chemical Co., Milwaukee, Wis.; dry powder blend dissolved in water to 0.9% NaCl) for thirty minutes at 37° C., removed, allowed to drip freely for thirty seconds, and re-weighed. The sample percent absorbency was then calculated using the formula: Absorbency (%)=(Wet Sample Weight−Dry Sample Weight)×100÷Dry Sample Weight. Results reported are the average of at least three replications.

Swell

Evaluation of swell was measured using the following test procedure. The width (W), length (L), and thickness (T) of an approximate 5.1-cm×5.1-cm dry sample were accurately measured. The sample was immersed in phosphate-buffered saline for thirty minutes at 37° C., removed, allowed to drip freely for thirty seconds, and all three dimensions of the sample were immediately re-measured. The sample percent swell was then calculated using the formula: Swell (%)= [W×L×T (Wet)−W×L×T(Dry)]×100÷W×L×T(Dry). Results reported are the average of at least three replications.

Moisture Vapor Transmission Rate (Standard "Dry" Method)

The "dry" moisture vapor transmission rate (MVTR) was measured according to ASTM E-96-80 using a modified Payne cup method. Specifically, a sample (3.5-cm diameter) was placed between adhesive-containing surfaces of two foil adhesive rings, each having a 2.54-cm diameter hole. The holes of each ring were carefully aligned. Finger pressure was used to form a foil/sample/foil assembly that was flat, wrinkle-free, and had no void areas in the exposed sample.

A 120-ml glass jar was filled to the halfway level with deionized water. The jar was fitted with a screw-on cap having a 3.8-cm diameter hole in the center thereof and with a 4.45-cm diameter rubber washer having a 2.84-cm diameter hole in its center. The rubber washer was placed on the lip of the jar and the foil/sample assembly was placed on the rubber washer. The lid was then screwed loosely on the jar.

The assembly was placed in a chamber at 38° C. and 20% relative humidity for four hours. At the end of four hours, the cap was tightened inside the chamber so that the sample was level with the cap (no bulging) and the rubber washer was in proper seating position.

The foil/sample assembly was then removed from the chamber and weighed immediately to the nearest 0.01 gram (initial weight $W_1$). The assembly was then returned to the chamber for at least 18 hours, after which it was removed and weighed immediately to the nearest 0.01 gram (final weight $W_2$). The MVTR in grams of water vapor transmitted per square meter of sample area in 24 hours was calculated according to the following formula (where "$T_1$" refers to exposure time in hours):

$$\text{"Dry" } MVTR = (W_1 - W_2)(4.74 \times 10^4) \div T_1$$

Three measurements of each sample were made, and the average value taken. The MVTR values are reported as $g/m^2/24$ hrs.

Moisture Vapor Transmission Rate (Inverted "Wet" Method)

The inverted "wet" MVTR was measured using the following test procedure. After obtaining the final "dry" weight ($W_2$) as described for the "dry" MVTR procedure, the assembly was returned to the chamber (38° C. and 20% relative humidity) for at least 18 additional hours with the sample jars inverted so that the deionized water was in direct contact with the test sample. The sample was then removed from the chamber and weighed to the nearest 0.01 gram (final "wet" weight, W3). The inverted "wet" MVTR in grams of water vapor transmitted per square meter of sample area in 24 hours was calculated according to the following formula (where "$T_2$" refers to exposure time in hours):

$$\text{Inverted "Wet" } MVTR = (W_2 - W_3)(4.74 \times 10^4) \div T_2$$

Three measurements of each sample were made, and the average value taken. The Inverted "Wet" MVTR values are reported as $g/m^2/24$ hrs.

Adhesive Starting Material

Adhesive 1 (Blown Micro Fiber (BMF)-Acrylate-PSA Web)

A porous polyacrylate-based BMF-PSA web was prepared using a melt blowing process similar to that described, for example, in Wente, Van A., "Superfine Thermoplastic Fibers," in *Industrial Engineering Chemistry*, Vol. 48, pages 1342 et seq (1956) or in Report No. 4364 of the Naval Research Laboratories, published May 25, 1954, entitled "Manufacture of Superfine Organic Fibers" by Wente, Van A.; Boone, C. D.; and Fluharty, E. L., except that the BMF apparatus utilized a single extruder which fed its extrudate to a gear pump that controlled the polymer melt flow. The gear pump fed a feedblock assembly that was connected to a melt-blowing die having circular smooth surface orifices (10/cm) with a 5:1 length to diameter ratio. The primary air was maintained at 220° C. and 241 KPa with a 0.076-cm gap width to produce a uniform web. The feedblock assembly was fed by a polymer melt stream (240° C.) comprised of isooctyl acrylate/acrylic acid/styrene macromer (IOA/AA/Sty, 92/4/4 ratio, Inherent Viscosity ~0.65 as measured by conventional means using a Cannon-Fenski #50 viscometer in a water bath controlled at 25° C. to measure the flow time of 10 ml of a polymer solution (0.2 g per deciliter polymer in ethyl acetate) PSA, prepared as described in Example 2 of U.S. Pat. No. 5,648,166 (Dunshee). Both the die and feedblock assembly were maintained at 220° C., and the die was operated at a rate of 178 g/hr/cm die width. The BMF-PSA web was collected on a double-coated silicone release paper (DCP-Lohja, Westchester, Ill.) which passed around a rotating drum collector at a collector to die distance of 17.8 cm. The resulting BMF-PSA web, comprising PSA microfibers having an average diameter of less than about 25 microns (as determined using a scanning electron microscope), had a basis weight of about 60 g/M$^2$.

Example 1

Foam/Fibrous-Adhesive/Film Composite

A sheet of 4.8-mm thick polyurethane foam (POLYCRIL™ 400, Fulflex, Inc., Middleton, R.I.) and 1.0-mil (25-microns) thick polyurethane film (extruded from a polyurethane resin available under the trade designation ESTANE 58237 from B.F. Goodrich, Cleveland, Ohio as described in U.S. Pat. No. 4,499,896 (Heinecke)) supported on standard MUL carrier paper (Schoeller Technical Papers, Pulaski, N.Y.) were laminated together with a center layer of the porous polyacrylate BMF-PSA web (Adhesive 1; release liner removed) using a laboratory laminator having two steel rollers with the bottom roller temperature set at 93° C. and the top roller temperature set at 149° C. The gap width between rollers was 0.3 mm, the nip pressure was 620 KPa, and the line speed was 122 cm/min. The resulting foam//fibrous-adhesive/film composite was cut into samples that were later used in absorbency, swell, and MVTR evaluations. Evaluation results are reported in Table 1.

Example 2

Foam/Fibrous-Adhesive/Film Pad//Fibrous-Adhesive//Nonwoven Dressing

The polyacrylate BMF-PSA web (Adhesive 1, including release liner) was laminated to a melt blown polyurethane nonwoven web (basis weight 100 g/m$^2$; prepared from MORTHANE PS-440 (Morton International, Seabrook, N.H.) as described in Example 1 of U.S. Pat. No. 5,230,701 (Meyer et al.), using a laboratory laminator having two steel rollers with the bottom roller temperature set at 93° C. and the top roller temperature set at 113° C. The gap width between rollers was 0.2 mm, the nip pressure was 620 KPa, and the line speed was 122 cm/min. The release liner was removed from the resulting fibrous-adhesive/nonwoven laminate and an island dressing was constructed by placing a 7.6-cm×7.6-cm pad of the foam/fibrous-adhesive/film composite of Example 1 in the center of a 10-cm×10-cm sample of the fibrous-adhesive/nonwoven laminate (film layer in direct contact with the adhesive layer) and applying light finger pressure to the pad to ensure good adhesion to the nonwoven layer. A 10-cm×10-cm standard J-fold silicone product release liner (DCP-Lohja, Westchester, Ill.) was placed over the foam layer and pressed against the adhesive layer to form the completed dressing. The dressing was then cut into samples that were later used in absorbency, swell, and MVTR evaluations. Evaluation results are reported in Table 1.

Example 3

Foam/Fibrous-Adhesive/Film Pad//Fibrous-Adhesive//Nonwoven Dressing

An island dressing was constructed as described in Example 2, except that a hydroentangled nonwoven polyester web (available under the trade designation SONTARA 8010 from Dupont, Wilmington, Del.) was substituted for the melt blown polyurethane nonwoven web, and the top roller temperature, during lamination, was set at 149° C. The resulting dressing was cut into samples that were later used in absorbency, swell, and MVTR evaluations. Evaluation results are reported in Table 1.

Example 4

Foam Pad//Fibrous-Adhesive//Nonwoven//Fibrous-Adhesive//Film Dressing

The polyacrylate BMF-PSA web (Adhesive 1, including release liner) was laminated to the melt blown polyurethane nonwoven web (basis weight 100 g/m$^2$; prepared from MORTHANE PS-440) as described in Example 2. The release liner was removed and the fibrous-adhesive/nonwoven laminate was further laminated (same conditions as described in Example 2, except the gap width was 0.3 mm) to a sheet of 1.0-mil thick polyurethane film (ESTANE 58237) on standard MUL carrier paper. The carrier paper was stripped off and the film/adhesive/nonwoven laminate was further laminated (same conditions as described in Example 2, except the bottom roller temperature was 93° C., the top roller temperature was 107° C., and the gap width was 0.3 mm) to the polyacrylate BMF-PSA web (Adhesive 1, including release liner) such that the nonwoven layer was in direct contact with the added adhesive layer. The release liner was removed from the resulting adhesive/nonwoven/adhesive/film laminate and an island dressing was constructed by placing a 7.6-cm×7.6-cm pad of 4.8-mm thick polyurethane foam (POLYCRIL 400) in the center of a 10-cm×10-cm sample of the laminate (film layer in direct contact with the adhesive layer) and applying light finger pressure to the pad to ensure good adhesion to the nonwoven layer. A 10-cm×10-cm standard J-fold silicone product release liner (DCP-Lohja, Westchester, Ill.) was placed over the foam layer and pressed against the adhesive layer to form the completed dressing. The dressing was then cut into samples that were later used in absorbency, swell, and MVTR evaluations. Evaluation results are reported in Table 1.

Example 5

Foam Pad//Fibrous-Adhesive//Film//Fibrous-Adhesive//Nonwoven Dressing

An island dressing was constructed as described in Example 4, except that the film/adhesive/nonwoven laminate was further laminated to the polyacrylate BMF-PSA web such that the film layer was in direct contact with the added adhesive layer. The completed dressing was cut into samples that were later used in absorbency, swell, and MVTR evaluations. Evaluation results are reported in Table 1.

Example 6

Foam Pad//Fibrous-Adhesive//Film//Nonwoven Dressing

A sheet of 1.0-mil (25-microns) thick polyurethane film (ESTANE 58237) on standard MUL carrier paper was heat laminated to a melt blown polyurethane nonwoven web (web as described in Example 2) using a laboratory laminator having two steel rollers with the bottom roller temperature set at 107° C. and the top roller temperature set at 141° C. The gap width between rollers was 0.2 mm, the nip pressure was 1378 KPa, and the line speed was 366 cm/min. The carrier paper was stripped off and the film/nonwoven laminate was further laminated to the polyacrylate BMF-PSA web (Adhesive 1, including release liner) such that the film layer was in direct contact with the adhesive layer. Lamination conditions were: bottom steel roller temperature—93° C., top steel roller temperature—107° C., gap width—0.3 mm, nip pressure—620 KPa, and line speed—122 cm/min. The release liner was removed from the resulting fibrous-adhesive/film/nonwoven laminate and an island dressing was constructed by placing a 7.6-cm× 7.6-cm pad of 4.8-mm thick polyurethane foam (POLYCRIL 400) in the center of a 10-cm×10-cm sample of the laminate (foam pad in direct contact with the adhesive layer) and applying light finger pressure to the pad to ensure good adhesion to the film layer. A 10 cm×10-cm standard J-fold silicone product release liner (DCP-Lohja) was placed over the foam layer and pressed against the adhesive layer to form the completed dressing. The dressing was then cut into samples that were later used in absorbency, swell, and MVTR evaluations. Evaluation results are reported in Table 1.

Example 7

Foam Pad//Fibrous-Adhesive//Nonwoven//Film Dressing

An island dressing was constructed as described in Example 6, except that the film/nonwoven laminate was further laminated to the polyacrylate BMF-PSA web such that the nonwoven layer was in direct contact with the adhesive layer. The completed dressing was cut into samples that were later used in absorbency, swell, and MVTR evaluations. Evaluation results are reported in Table 1.

Example 8

Foam(Internal Pad) Pad//Fibrous-Adhesive// Nonwoven//Fibrous-Adhesive//Film Dressing An island dressing was constructed as described in Example 4, except that the composite contained a 5-cm×5-cm internal pad of blended nonwoven rayon/"Oasis" superabsorbent fibers (National Nonwovens, Cincinnati, Ohio) in order to enhance the absorbent capacity of the composition. Specifically, after removal of the release liner from the adhesive/nonwoven/adhesive/film laminate (as described in Example 4), the polyurethane foam pad was placed directly over the internal pad that had been placed in the center of the laminate. The outer edge of the foam pad extended beyond the entire perimeter of the internal pad and was adhered to the adhesive surface of the laminate by applying finger pressure to the foam pad. The foam pad thus entirely encompassed the internal pad. A standard J-fold silicone product release liner was placed over the foam layer and pressed against the adhesive layer to form the completed dressing. The dressing was then cut into samples that were later used in absorbency, swell, and MVTR evaluations. Evaluation results are reported in Table 1.

Example 9

Foam(Internal Pad) Pad//Fibrous-Adhesive//Film// Fibrous-Adhesive//Nonwoven Dressing An island dressing was constructed as described in Example 5, except that the composite contained a 5-cm×5-cm internal pad of blended nonwoven rayon/"Oasis" superabsorbent fibers (National Nonwovens) in order to enhance the absorbent capacity of the composition. The internal pad was built into the composition as described in Example 8. The completed dressing was then cut into samples that were later used in absorbency, swell, and MVTR evaluations. Evaluation results are reported in Table 1.

Example 10

Foam(Internal Pad) Pad//Fibrous-Adhesive//Film// Nonwoven Dressing

An island dressing was constructed as described in Example 6, except that the composite contained a 5-cm×5-cm internal pad of blended nonwoven rayon/"Oasis" superabsorbent fibers (National Nonwovens) in order to enhance the absorbent capacity of the composition. The internal pad was built into the composition as described in Example 8. The completed dressing was then cut into samples that were later used in absorbency, swell, and MVTR evaluations. Evaluation results are reported in Table 1.

Example 11

Foam(Internal Pad) Pad//Fibrous-Adhesive// Nonwoven//Film Dressing

An island dressing was constructed as described in Example 7, except that the composite contained an internal pad of blended nonwoven rayon/"Oasis" superabsorbent fibers (National Nonwovens) in order to enhance the absorbent capacity of the composition. The internal pad was built into the composition as described in Example 8. The completed dressing was then cut into samples that were later used in absorbency, swell, and MVTR evaluations. Evaluation results are reported in Table 1.

Example 12

Foam Pad//Fibrous-Adhesive//Nonwoven//Fibrous-Adhesive//Film Dressing

An island dressing was constructed as described in Example 4, except that a hydroentangled nonwoven polyester web (SONTARA 8010, Dupont) was substituted for the melt blown polyurethane nonwoven web, and the top roller temperature, during lamination of the polyacrylate adhesive to the nonwoven, was set at 149° C. The resulting dressing was cut into samples that were later used in absorbency, swell, and MVTR evaluations. Evaluation results are reported in Table 1.

Example 13

Foam Pad//Fibrous-Adhesive//Nonwoven//Fibrous-Adhesive//Film Dressing

An island dressing was constructed as described in Example 12, except that a hydroentangled, nonwoven rayon (30%)/polyester (70%) web (SONTARA 8411, Dupont) was substituted for the SONTARA 8010 web. The completed dressing was then cut into samples that were later used in absorbency, swell, and MVTR evaluations. Evaluation results are reported in Table 1.

Example 14

Foam Pad//Fibrous-Adhesive//Film//Fibrous-Adhesive//Nonwoven Dressing

An island dressing was constructed as described in Example 12, except that the film/adhesive/nonwoven laminate was further laminated to the polyacrylate adhesive such that the film layer was in direct contact with the outer adhesive layer. The completed dressing was cut into samples that were later used in absorbency, swell, and MVTR evaluations. Evaluation results are reported in Table 1.

Example 15

Foam(Internal Pad) Pad//Fibrous-Adhesive//Nonwoven//Fibrous-Adhesive//Film Dressing An island dressing was constructed as described in Example 12, except that the composite contained a 5-cm× 5-cm internal pad of blended nonwoven rayon/"Oasis" superabsorbent fibers (National Nonwovens) in order to enhance the absorbent capacity of the composite. The internal pad was built into the composite as described in Example 8. The completed dressing was then cut into samples that were later used in absorbency, swell, and MVTR evaluations. Evaluation results are reported in Table 1.

Example 16

Foam(Internal Pad) Pad//Fibrous-Adhesive//Nonwoven//Fibrous-Adhesive//Film Dressing An island dressing was constructed as described in Example 13, except that the composite contained a 5-cm× 5-cm internal pad of blended nonwoven rayon/"Oasis" superabsorbent fibers (National Nonwovens) in order to enhance the absorbent capacity of the composite. The internal pad was built into the composite as described in Example 8. The completed dressing was then cut into samples that were later used in absorbency, swell, and MVTR evaluations. Evaluation results are reported in Table 1.

Example 17

Foam(Internal Pad) Pad//Fibrous-Adhesive//Film//Fibrous-Adhesive//Nonwoven Dressing An island dressing was constructed as described in Example 14, except that the composite contained a 5-cm× 5-cm internal pad of blended nonwoven rayon/"Oasis" superabsorbent fibers (National Nonwovens) in order to enhance the absorbent capacity of the composite. The internal pad was built into the composite as described in Example 8. The completed dressing was then cut into samples that were later used in absorbency, swell, and MVTR evaluations. Evaluation results are reported in Table 1.

Example 18

Foam Pad//Adhesive//Film Dressing

An island dressing was constructed as described in U.S. Pat. No. 5,738,642 (Heinecke, et. al.) utilizing a conventional adhesive similar to those described in U.S. Pat. No. 4,871,812 (Lucast et. al.) (except adhesive was reinforced with 1% polyethyloxazoline as opposed to the indicated 1.5–8%). The release liner was removed from the adhesive-coated film and the dressing was completed by placing a 7.6-cm×7.6-cm pad of 4.8-mm thick polyurethane foam (POLYCRIL 400) in the center of a 10-cm×10-cm sample of the backing and applying light finger pressure to the pad to ensure good adhesion to the film layer.

Example 19

Foam(Internal Pad) Pad//Adhesive//Film Dressing

An island dressing was constructed as described in Example 18, except that the composite contained a 5-cm× 5-cm internal pad of blended nonwoven rayon/"Oasis" superabsorbent fibers (National Nonwovens) in order to enhance the absorbent capacity of the composite. The internal pad was built into the composite as described in Example 8. The completed dressing was then cut into samples that were later used in absorbency, swell, and MVTR evaluations. Evaluation results are reported in Table 1.

Example 20

Foam Materials

The following commercial foam materials were cut into samples and evaluated for absorbency and swell: foams available under the trade designations HYDRASORB (HYPOL) from W.R. Grace & Co., Columbia, Md., EPI-LOCK from Calgon/Vestal Laboratories, St. Louis, Mo., LYOFOAM from ConvaTec, Skillman, N.J.), and POLYCRIL 400 from Fulflex, Inc. Results are reported in Table 2.

Test Data

Dressings from Examples 1–19 were cut into appropriate sample sizes and evaluated for water absorbency, swell, "Dry" MVTR, and "Wet" MVTR. The results are shown in Table 1 along with results for four commercial adhesive-containing foam dressings, ALLEVYN Adhesive (Smith & Nephew, York, England), POLYMEM Membrane adhesive dressing (Ferris Mfg. Co., Burr Ridge, Ill.), LyoFoam A (ConvaTec, Skillman, N.J.), and Tielle (Johnson & Johnson, Arlington, Tex.).

TABLE 1

| Example | Saline Water Absorbency (%) | Swell (%) | Dry MVTR (g/m$^2$/24 hr) | Wet MVTR (g/m$^2$/24 hr) |
|---|---|---|---|---|
| 1 | 924 | 6 | 1738 | 15,175 |
| 2 | 655 | 6 | 825 | 5859 |
| 3 | 683 | 6 | 1685 | 18,782 |
| 4 | 825 | 6 | 1729 | 13,443 |
| 5 | 675 | 6 | 1641 | 15,563 |
| 6 | 678 | 6 | 2449 | 19,658 |
| 7 | 754 | 6 | 2467 | 26,748 |
| 8 | 853 | 6 | 1703 | 8177 |
| 9 | 916 | 6 | 1668 | 33,825 |
| 10 | 964 | 6 | 2194 | 18,061 |
| 11 | 968 | 6 | 2265 | 11,988 |
| 12 | 703 | 6 | 1729 | 15,695 |
| 13 | 912 | 7 | 1647 | 14,907 |
| 14 | 764 | 6 | 1729 | 17,459 |
| 15 | 998 | 6 | 1712 | 15,800 |
| 16 | 1023 | 5 | 1530 | 14,439 |
| 17 | 1041 | 6 | 1720 | 32,930 |
| 18 | 496 | 1 | 740 | 1277 |
| 19 | 1143 | −7 | 825 | 2132 |
| ALLEVYN Adhesive | 600–800 | 30 | 400–500 | 500–600 |
| POLYMEM Membrane | 500 | 60 | 500 | 600 |
| LYOFOAM A | 100 | 50 | 300 | 900 |
| Tielle | 700 | 250 | 1900 | 2350 |

TABLE 2

| Foam Sample (Example 20) | Buffered Saline Absorbency (%) | Swell (%) |
|---|---|---|
| HYDRASORB | 1367 | 89 |
| EPI-LOCK | 1434 | 90 |

TABLE 2-continued

| Foam Sample (Example 20) | Buffered Saline Absorbency (%) | Swell (%) |
|---|---|---|
| LYOFOAM | 218 | 11 |
| POLYCRIL 400 | 1089 | 8 |

As shown in Table 1, composite dressings of the present invention (Examples 1–19) all had swell values less than 10%. In contrast, the commercial dressings had swell values in the range of 30–250%. Additionally, the composite dressings of the present invention had dry MVTR values less than 2500 g/m$^2$/24 hours, and in some cases less than 2000 g/m$^2$/24 hours; and, except for Examples 18–19 that used a film continuously coated with adhesive, had wet MVTR values of greater than 5000 g/m$^2$/24 hours. The data from Table 2 show that among the four foam samples evaluated, only POLYCRIL 400 had low swell (8%) coupled with high absorbency (1089%).

All patents, patent applications and publications are incorporated by reference herein as though individually incorporated by reference. Various modifications and alterations of this invention will become apparent to those skilled in the art without departing from the scope and spirit of this invention, and it should be understood that this invention is not to be unduly limited to the illustrative embodiments set forth herein.

What is claimed is:

1. A medical article comprising a backing, an absorbent foam, and a fibrous adhesive comprising a nonwoven web of intimately entangled coherent pressure sensitive adhesive fibers disposed between the backing and the absorbent foam, wherein the backing comprises a liquid-impervious, moisture-vapor permeable polymeric film.

2. The medical article of claim 1 wherein the foam is substantially nonswellable.

3. The medical article of claim 2 wherein the substantially nonswellable foam increases in volume by no greater than about 10% following a 30-minute soaking in phosphate buffered saline at 37° C.

4. The medical article of claim 1 which has a dry MVTR of less than about 2000 g/m$^2$/24 hours and a wet MVTR of at least about 3000 g/m$^2$/24 hours at 38° C. and 20% relative humidity.

5. The medical article of claim 1 wherein the foam absorbs greater than 250 wt-% aqueous saline solution when immersed in phosphate buffered saline containing 0.9 wt-% NaCl at 37° C. for 30 minutes.

6. The medical article of claim 1 wherein the fibrous adhesive comprises a polyacrylate.

7. A medical article comprising a backing, an absorbent, substantially nonswellable foam, and an adhesive disposed therebetween.

8. A medical article comprising a backing, a foam, and a fibrous adhesive comprising a nonwoven web of intimately entangled coherent pressure sensitive adhesive fibers disposed between the backing and the foam.

9. The medical article of claim 8 wherein the pressure sensitive adhesive fibers are 100 microns or less in diameter.

10. The medical article of claim 8 wherein the fibrous adhesive comprises a polyacrylate.

\* \* \* \* \*

UNITED STATES PATENT AND TRADEMARK OFFICE
CERTIFICATE OF CORRECTION

PATENT NO. : 6,881,875 B2  Page 1 of 1
APPLICATION NO. : 10/351932
DATED : April 19, 2005
INVENTOR(S) : Mary M. Swenson It is certified that error appears in the above-identified patent and that said Letters Patent is hereby corrected as shown below:

Title Page,
Under Foreign Patent Documents, please add:
    0 452 470    10/23/91    EPO
    WO 91/06323    05/16/91    PCT
    WO 96/10972    04/18/96    PCT
    WO 99/19410    04/22/99    PCT
    WO 99/27975    06/10/99    PCT
    WO 99/28539    06/10/99    PCT
    WO 99/28540    06/10/99    PCT Column 9,
Line 15, delete "60 g/$M^2$." and insert in place thereof --60 g/$m^2$.--.
Line 31, delete "foam//" and insert in place thereof --foam/--.

Signed and Sealed this

Thirty-first Day of July, 2007

JON W. DUDAS
*Director of the United States Patent and Trademark Office*